United States Patent [19]

Lawate

[11] Patent Number: 5,451,332
[45] Date of Patent: Sep. 19, 1995

[54] ESTOLIDES OF HYDROXY-CONTAINING TRIGLYCERIDES THAT CONTAIN A PERFORMANCE ADDITIVE

[75] Inventor: Saurabh S. Lawate, Concord, Ohio

[73] Assignee: The Lubrizol Corporation, Wickliffe, Ohio

[21] Appl. No.: 188,263

[22] Filed: Jan. 28, 1994

[51] Int. Cl.⁶ ......................................... C10M 141/02
[52] U.S. Cl. .............................. 252/32.7 E; 252/49.8; 252/49.9; 252/50; 252/56 S; 252/56 R
[58] Field of Search ..................... 252/56 S, 56 R, 50, 252/49.9, 32.7 E, 49.8, 52 R

[56] References Cited

U.S. PATENT DOCUMENTS

| | | | |
|---|---|---|---|
| 844,426 | 2/1907 | Twitchell | 554/165 |
| 2,049,072 | 7/1936 | Mikeska et al. | 87/9 |
| 2,156,737 | 5/1939 | Priester | 260/413 |
| 2,652,410 | 9/1953 | Cunningham et al. | 260/404.5 |
| 2,652,411 | 9/1953 | Teeter et al. | 260/405 |
| 2,877,181 | 3/1959 | Dilworth et al. | 252/40.5 |
| 3,634,245 | 1/1972 | Meisters | 252/49.3 |
| 3,720,695 | 3/1973 | Meisters | 260/404.8 |
| 3,909,425 | 9/1975 | Crawford et al. | 252/32.7 |
| 3,928,401 | 12/1975 | Sturwold et al. | 252/56 S |
| 4,067,817 | 1/1978 | Sturwold | 252/49.3 |
| 4,582,715 | 4/1986 | Volpenhein | 426/601 |
| 4,755,316 | 7/1988 | Magid et al. | 252/52 A |
| 4,769,178 | 9/1988 | Kenmochi et al. | 252/56 |
| 4,783,274 | 11/1988 | Jokinen et al. | 252/56 S |
| 4,885,104 | 12/1989 | Sturwold | 252/56 S |
| 5,037,564 | 8/1991 | Nishizaki et al. | 252/22 |
| 5,145,593 | 9/1992 | Takashima | 252/56 |
| 5,151,205 | 9/1992 | Culpon, Jr. | 252/51.5 |
| 5,298,177 | 3/1994 | Stoffa | 252/18 |

*Primary Examiner*—Jacqueline V. Howard
*Attorney, Agent, or Firm*—James L. Cordek; Frederick D. Hunter; Joseph P. Fischer

[57] ABSTRACT

A composition comprising;

(A) at least one triglyceride estolide of the formula

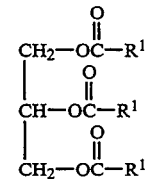

wherein $R^1$ is an aliphatic group or an aliphatic group containing an ester moiety $R^2COO-$ with the proviso that at least one $R^1$ is an aliphatic group containing the ester moiety, and contains from about 5 to about 23 carbon atoms, and $R^2$ is a hydrocarbyl group containing from 1 to 100 carbon atoms and (B) at least one performance additive.

13 Claims, No Drawings

ESTOLIDES OF HYDROXY-CONTAINING TRIGLYCERIDES THAT CONTAIN A PERFORMANCE ADDITIVE

FIELD OF THE INVENTION

The present invention relates to estolides of hydroxy-containing triglycerides that have enhanced performance. This enhanced performance is brought about by the addition of a performance additive. Performance areas that are improved are anti-wear, oxidation inhibition, rust/corrosion inhibition, metal passivation, extreme pressure, friction modification, viscosity modification, foam inhibition, emulsification, demulsification, lubricity, dispersancy, detergency and the like.

BACKGROUND OF THE INVENTION

Successful use of estolides of hydroxy-containing triglycerides as environmentally friendly, that is, biodegradable base fluids in industrial applications is contingent upon increasing the performance values as stated above. In many industrial applications these values of the estolide are too poor to be of practical use. In order to take advantage of the biodegradability of estolides, it becomes necessary to increase the performance values.

U.S. Pat. No. 844,426 (Twitchell, Feb. 19, 1907) relates to a process for manufacturing certain organic products. One of the reactants contains an alcoholic hydroxyl, of which castor oil is cited, and the other reactant is a fatty acid such as stearic and oleic acids. The reaction takes place in the presence of a catalyst described as containing a sulfa fatty acid group.

U.S. Pat. No. 2,156,737 (Priester, May 2, 1939) relates to the preparation or production of unsaturated fatty acids of the type containing two double bonds and to the preparation of an intermediate product from which said unsaturated fatty acids may be derived.

More particularly stated, this reference relates to a process for the preparation of 9,11-octadecadiene 1-acid from ricinoleic acid. The ricinoleic acid is both pure ricinoleic acid or ricinoleic acid obtained from castor oil of which the latter being obtained by the splitting up of castor oil.

U.S. Pat. No. 2,049,072 (Mikeska et al, Jul. 28, 1936) relates to the preparation of lubricants by blending with a mineral oil the product obtained by esterification of hydroxy groups in natural or synthetic fatty acids or glycerides, with special reference to castor oil, with or without subsequent stabilizations of said esterified product as by hydrogenation.

U.S. Pat. No. 2,652,410 (Cunningham et al, Sep. 15, 1953) relates to methods for reacting alpha-hydroxy acids and/or estolides with polyhydric alcohols. More particularly, this reference relates to methods for esterifying and dehydroxylating alpha-hydroxy acids and/or estolides such as are obtained by the controlled oxidation of paraffin wax.

U.S. Pat. No. 2,877,181 (Dilworth et al, Mar. 10, 1959) relates to anhydrous calcium fatty acid greases. More particularly, this reference discloses an additive that stabilizes anhydrous calcium fatty acid greases. This additive is an estolide and the estolides which act as stabilizers are intermolecular esters and polyesters of $C_{10}$ to $C_{24}$ hydroxy fatty acids having the general formula

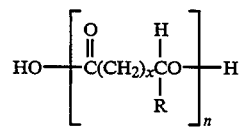

wherein R is an aliphatic hydrocarbon radical containing 1 to 21 carbon atoms, x is an integer having a value to 1 to 21 and n is an integer having a value of to about 12.

U.S. Pat. No. 4,582,715 (Volpenhein, Apr. 15, 1986) relates to alpha acrylated glycerides of the formula:

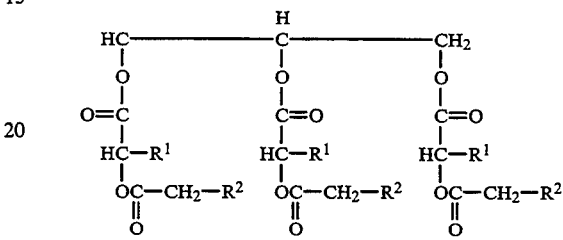

wherein each $R^1$ is a $C_{10}$–$C_{14}$ alkyl group and wherein each $R^2$ is a $C_{14}$–$C_{16}$ aliphatic group.

SUMMARY OF THE INVENTION

A composition is disclosed which comprises
(A) at least one triglyceride estolide of the formula

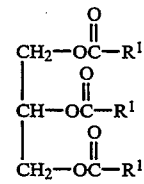

wherein $R^1$ is an aliphatic group or an aliphatic group containing an ester moiety $R^2COO$— with the proviso that at least one $R^1$ is an aliphatic group containing the ester moiety, and contains from about 5 to about 23 carbon atoms, and $R^2$ is a hydrocarbyl group containing from 1 to 100 carbon atoms and
(B) a performance additive.

DETAILED DESCRIPTION OF THE INVENTION (A) The Triglyceride Estolide

An estolide is the product formed by the esterification reaction of a hydroxy-containing fatty acid and a carboxylic acid.

The esterification to form the estolide occurs at a temperature of from ambient up to the decomposition temperature of any reactant or product. Usually the upper temperature limit is not more than 150° C. and preferably not more than 120° C. To shift the equilibrium to the right when forming an estolide, it is necessary to use either a large excess of carboxylic acid, or else remove water as it is formed. In either case, excess carboxylic acid or formed water can be removed by distillation.

As an example, under proper conditions the —OH from one ricinoleic acid molecule can react with the —COOH of another ricinoleic acid molecule to give an estolide:

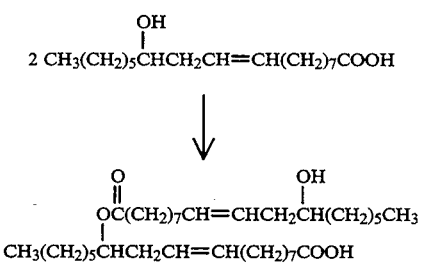

This estolide would continue to crosslink or react linearly at the unreacted —OH and —COOH sites to form a polyestolide.

In this invention, component (A) is a triglyceride estolide of the formula

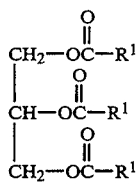

wherein $R^1$ is an aliphatic group or an aliphatic group containing an ester moiety $R^2COO$— with the proviso that at least one $R^1$ is an aliphatic group containing the ester moiety, and contains from about 5 to about 23 carbon atoms, and $R^2$ is a hydrocarbyl group containing from 1 to 100 carbon atoms.

The aliphatic group $R^1$ is alkyl such as pentyl, heptyl, nonyl, undecyl, tridecyl, heptadecyl; alkenyl containing a single bond such as heptenyl, nonenyl, undecenyl, tridecenyl, heptadecenyl, nonadecenyl, heneicosenyl; alkenyl containing 2 or 3 double bonds such as 8,11-heptadecadienyl and 8,11,14-heptadecatrienyl. All isomers of these are included, but straight chain groups are preferred.

At least one of the $R^1$ groups contains the ester moiety $R^2COO$—. The residue of this $R^1$ group (the $R^1$ as described above less the hydrogen and also less the $R^2COO$—) is still defined as an aliphatic group and as such is defined by the parameters of the aliphatic groups above. An example of an $R^1$ containing the ester moiety is

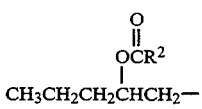

Removing the $R^2COO$— from this structure gives

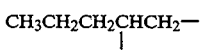

a residue which is defined as an aliphatic group.

The hydrocarbyl group $R^2$ includes the following:

(1) Aliphatic hydrocarbon groups; that is, alkyl groups such as heptyl, nonyl, undecyl, tridecyl, heptadecyl; alkenyl groups containing a single double bond such as heptenyl, nonenyl, undecenyl, tridecenyl, isostearyl, heptadecenyl, heneicosenyl; alkenyl groups containing 2 or 3 double bonds such as 8,11-heptadecadienyl and 8,11,14-heptadecatrienyl. All isomers of these are included, but straight chain groups are preferred.

(2) Substituted aliphatic hydrocarbon groups; that is groups containing non-hydrocarbon substituents which, in the context of this invention, do not alter the predominantly hydrocarbon character of the group. Those skilled in the art will be aware of suitable substituents; examples are hydroxy, carbalkoxy, (especially lower carbalkoxy) and alkoxy (especially lower alkoxy), the term, "lower" denoting groups containing not more than 7 carbon atoms.

(3) Hetero groups; that is, groups which, while having predominantly aliphatic hydrocarbon character within the context of this invention, contain atoms other than carbon present in a chain or ring otherwise composed of aliphatic carbon atoms. Suitable hetero atoms will be apparent to those skilled in the art and include, for example, oxygen, nitrogen and sulfur.

At least one of the $R^1$ groups is an aliphatic group containing an ester moiety $R^2COO$—. In a preferred embodiment $R^1$ is

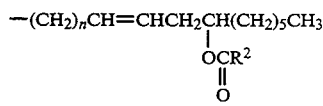

wherein n is from 5 to 13 and $R^2$ is an aliphatic group containing 1 to 23 carbon atoms, preferably from 3 to 17 carbon atoms.

The triglyceride estolide (A) is prepared by reacting a triglyceride that contains at least one —OH group with a carboxylic acid $R^2COOH$. At least 1 up to 3 —OH groups are present in the triglyceride. For each —OH group present, there is employed one mole of carboxylic acid.

Triglycerides containing —OH groups occur in nature as castor oil wherein n is 7 and contains three —OH groups and lesquerella oil wherein n is 9 and contains two —OH groups.

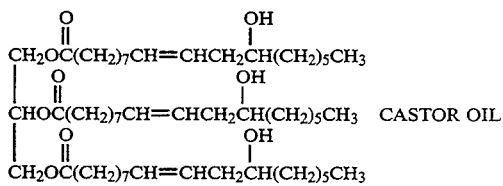

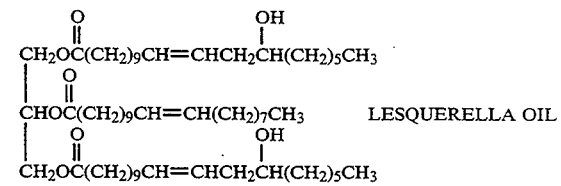

The chemical profiles of castor oil and lesquerella oil contain triglycerides other than those of the structures outlined above. A triglyceride of ricinoleic acid is the predominate triglyceride of castor oil and is present at from 80–89% by weight. A triglyceride of 2 moles 14-hydroxy-11-eicosenoic acid and 1 mole 11-eicosenoic acid is the predominate triglyceride of lesquerella oil and is generally present in lesquerella oil in an amount in excess of 50% by weight.

The carboxylic acid R²COOH reacted with the hydroxy-containing triglyceride contains from 2 to 24 carbon atoms (acetic acid to tetracosanoic acid) including isomers and unsaturation. Preferred carboxylic acids are the acids of butyric, caproic, caprylic, capric, lauric, myristic, palmitic, stearic, oleic, linoleic, and linolenic.

The esterification to make the triglyceride estolide occurs by reacting a carboxylic acid with the hydroxy containing triglyceride. One mole of carboxylic acid is employed for every -OH group present in the hydroxy-containing triglyceride.

The following examples are illustrative of the preparation of triglyceride estolides wherein the carboxylic acid is a monocarboxylic acid. Unless otherwise indicated, all parts and percentages are by weight. Solvents may or may not be employed. Optionally, the obtained estolides are refined and bleached.

Example A-1

Added to a 1 liter, 4 neck flask are 200 parts (0.19 moles) of castor oil, 74.2 parts (0.57 moles) heptanoic acid, 300 ml xylene and 2.5 parts paratoluenesulfonic acid. The contents are heated to 150° C. with stirring during which time water is azeotroped off. Xylene is stripped off using a nitrogen sweep and later to 12 millimeters mercury. The contents are filtered to give the desired product.

Example A-2

Lesquerella oil and heptanoic acid are reacted on a (1 —OH: 1 —COOH) basis. The lesquerella oil, heptanoic acid, para-toluenesulfonic acid and xylene are added to a flask and the procedure of Example A-1 is essentially followed. The filtrate is the desired product.

Example A-3

Lesquerella oil and isostearic acid are reacted on a (1 —OH: 1 —COOH) basis. The lesquerella oil, isostearic acid, xylene and methanesulfonic acid are added to a flask and the procedure of Example A-1 is essentially followed. The filtrate is the desired product.

Example A-4

Lesquerella oil and oleic acid are reacted on a (1 —OH: 1 —COOH) basis. The lesquerella oil, oleic acid, xylene and methanesulfonic acid are added to a flask and the procedure of Example A-1 is essentially followed. The filtrate is the desired product.

Mono carboxylic acids are also formed by the hydrolysis of a triglyceride.

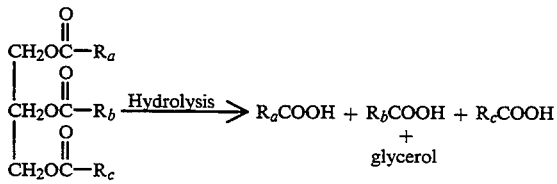

In the above reactions $R_a$, $R_b$ and $R_c$ are the same or different and contain from 1 to 23 carbon atoms.

The following example is directed to the preparation of a triglyceride estolide wherein the monocarboxylic acid is obtained from the hydrolysis of a triglyceride.

Example A-5

Added to a 12 liter, 4 neck flask are 3129 parts Sunyl 87, 3000 parts water and 1000 parts isopropyl alcohol. The mixture is heated to 60° C. and added is 100 parts of a 50% aqueous solution of sodium hydroxide. The sodium hydroxide solution is added in 50 millimeter portions. This addition is exothermic and cooling is required to keep the reaction under control. At the end of this addition, the contents are permitted to continue stirring for 6 hours. At 60° C. concentrated aqueous hydrochloric acid (37%) is slowly added until a pH of 2 is reached. At the end of this addition, the contents are permitted to stir for 30 more minutes. Stirring is halted and the contents separate into layers. The bottom (aqueous) portion is removed and discarded and the remainder of the contents is washed three times with 1000 parts hot water. After the third wash, the water layer is removed and discarded and the contents are stripped and filtered to give a monocarboxylic acid mixture containing 87% oleic acid.

In a separate flask are added lesquerella oil and the 87% oleic acid on a 1 —OH:1 —COOH basis, along with para-toluenesulfonic acid and xylene. The contents are heated to 150° C. with stirring while azeotroping off water. The contents are then stripped and filtered to give the desired product.

In another embodiment, acids other than aliphatic mono-carboxylic acids may be reacted with the hydroxy containing triglyceride to form an estolide. These may be aliphatic dicarboxylic acids or aryl mono-, di- or tri- carboxylic acids. Aliphatic dicarboxylic acids are of the formula HOOCCH=CHCOOH or HOOC(CH$_2$)$_t$COOH wherein t is from zero up to 8. Envisioned within the formula HOOCCH=CHCOOH are maleic acid and fumaric acid. The aliphatic dicarboxylic acids of interest are: oxalic acid, malonic acid, succinic acid, glutaric acid, adipic acid, pimelic acid, suberic acid, azelaic acid and sebacic acid. One —COOH of component (B) is employed for each —OH group present within component (A).

The aryl carboxylic acids are of the formula Ar(-COOH)$_x$ wherein Ar is a benzene or naphthalene nucleus and x is 1, 2 or 3. Aryl carboxylic acids having utility in this invention are benzoic acid, phthalic acid, isophthalic acid, terephthalic acid, 1,2,3,-benzenetricarboxylic acid, 1,2,4-benzenetricarboxylic acid, 1,3,5-benzenetricarboxylic acid, and the various isomers of the mono-, di- and tri- naphthoic acids. Again one —COOH of component (B) is employed for each —OH group present within component (A).

As stated earlier, one way of shifting the equilibrium to the right is to employ excess carboxylic acid. After the estolide is formed the excess carboxylic acid can be distilled out or the carboxylic acid can be reacted with a basic compound to form a salt which is then separated out.

Examples of the formation of estolides utilizing aliphatic dicarboxylic acids or aryl mono-, di, or tri-carboxylic acids are as follows.

Example A-6

Added to a 2 liter, 4 neck flask are 457 parts lesquerella oil, 58 parts fumaric acid, 4 parts methanesulfonic acid and 250 parts xylene. The lesquerella oil and fumaric acid are charged on a 1 —OH:1 —COOH basis. Mixing is begun at room temperature and it is noted, that the fumaric acid remains insoluble. The contents are heated to effect solution. The temperature is increased to 150° C. and held for 16 hours during which time 9 ml of water is obtained. Solvent is removed first by nitrogen sweeping and finally under vacuum of 25 millimeters mercury. At 70° C. the contents are filtered to give the desired product.

Example A-7

Following the procedure of Example A-6, 457 parts lesquerella oil, 54.6 parts adipic acid, 5 parts para-toluenesulfonic acid and 400 parts xylene are reacted at 150° C. The contents are stripped and filtered to give the desired product.

Example A-8

The procedure of Example A-6 is repeated except that fumaric acid is replaced with maleic acid.

Example A-9

Following the procedure of Example A-6, 457 parts lesquerella oil, 94 parts azelaic acid, 8 parts para-toluenesulfonic acid and 500 parts xylene are reacted at 150° C. The contents are stripped and filtered to give the desired product.

Example A-10

Following the procedure of Example A-6, 457 parts lesquerella oil, 84 parts phthalic acid, 7 parts para-toluenesulfonic acid and 400 parts xylene are reacted at 150° C. The contents are stripped and filtered to give the desired product.

Example A-11

The procedure of Example A-10 is repeated except that phthalic acid is replaced with isophthalic acid.

Example A-12

The procedure of Example A-10 is repeated except that phthalic acid is replaced with terephthalic acid.

Example A-13

Following the procedure of Example A-6, 457 parts lesquerella oil, 105 parts hemimellitic acid, 10 parts para-toluenesulfonic acid and 500 parts xylene are reacted at 150° C. The contents are stripped and filtered to give the desired product.

Example A-14

The procedure of Example A-13 is repeated except that hemimellitic acid is replaced with trimellitic acid.

Example A-15

The procedure of Example A-13 is repeated except that hemimellitic acid is replaced with trimesic acid.

(B) The Performance Additive

In addition to component (A), the compositions of this invention also include (B), a performance additive. The performance enhanced by these additives in the areas of anti-wear, oxidation inhibition, rust/corrosion inhibition, metal passivation, extreme pressure, friction modification, viscosity modification, foam inhibition, emulsification, demulsification, lubricity, dispersancy and detergency and the like.

The performance additive (B) is selected from the group consisting of
(1) an alkyl phenol,
(2) a benzotriazole,
(3) a phosphatide,
(4) an amine phosphate,
(5) citric acid or its derivative,
(6) a triphenyl phosphorothionate,
(7) a viscosity index improver, and
(8) an aromatic amine.

(B)(1) The Alkyl Phenol

Component (B-1) is an alkyl phenol of the formula

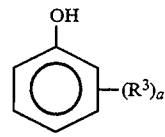

wherein $R^3$ is an alkyl group containing from 1 up to about 24 carbon atoms and a is an integer of from 1 up to 5. Preferably $R^3$ contains from 4 to 18 carbon atoms and most preferably from 4 to 12 carbon atoms. $R^3$ may be either straight chained or branched chained and branched chained is preferred. The preferred value for a is an integer of from 1 to 4 and most preferred is from 1 to 3. An especially preferred value for a is 2. When a is less than 5, it is preferred that the position para to the OH group be open.

Mixtures of alkyl phenols may be employed. Preferably the phenol is a butyl substituted phenol containing 2 or 3 t-butyl groups. When a is 2, the t-butyl groups occupy the 2,6-position, that is, the phenol is sterically hindered:

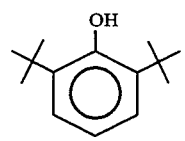

When a is 3, the t-butyl groups occupy the 2,4,6-position.

(B)(2) The Benzotriazole

The benzotriazole compound is of the formula

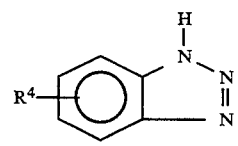

wherein $R^4$ is hydrogen a straight or branched-chain alkyl group containing from 1 up to about 24 carbon atoms, preferably 1 to 12 carbon atoms and most preferably 1 carbon atom. When $R^4$ is 1 carbon atom the benzotriazole compound is tolyltriazole of the formula

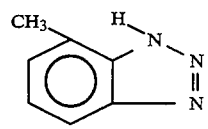

Tolyltriazole is available under the trade name Cobratec TT-100 from Sherwin-Williams Chemical.

(B)(3) The Phosphatide

The phosphatide is of the formula

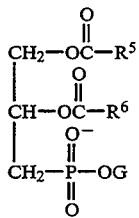

wherein $R^5$ and $R^6$ are aliphatic hydrocarbyl groups containing from 8 to about carbon atoms and G is selected from the group consisting of hydrogen,

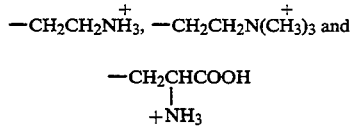

such that the phosphatide is lecithin. Particularly effective phosphatides are soybean lecithin, corn lecithin, peanut lecithin, sunflower lecithin, safflower lecithin and rapeseed lecithin.

(B)(4) The Amine Phosphate

The amine phosphates having utility in this invention are liquid amine phosphates that are $C_{11}$–$C_{14}$ branched alkylamines, monohexyl and dihexyl phosphates. A preferred amine phosphate is available from Ciba-Geigy under the name Irgalube ®349.

(B)(5) The Citric Acid and its Derivatives

The citric acid or derivatives of citric acid are of the formula

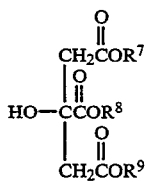

wherein $R^7$, $R^8$ and $R^9$ are independently hydrogen or aliphatic hydrocarbyl groups containing from 1 to about 12 carbon atoms, with the proviso that at least one of $R^7$, $R^8$ and $R^9$ is an aliphatic hydrocarbyl group and preferably contains from 1 to about 6 carbon atoms.

(B)(6) The Triphenyl Phosphorothionate

Component (B)(6) is a triphenyl phosphorothionate of the formula

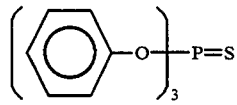

that is the reaction product of triphenylphosphite and sulfur. This component is commercially available from Ciba-Geigy under the name Irgalube ®TPPT.

(B)(7) The Viscosity Index Improver

Viscosity Index or "V.I." is an arbitrary number which indicates the resistance of a lubricant to viscosity change with temperature. The Dean and Davis viscosity index calculated from the observed viscosities of a lubricant at 40° C. and 100° C. gives V.I. values ranging from 0 or negative values to values of 200 or more. The higher its V.I. value, the greater the resistance of a lubricant to thicken at low temperatures and thin out at high temperatures.

An ideal lubricant for most purposes would possess the same viscosity at all temperatures. All lubricants depart from this ideal, some more than others. For example, lubricating oils derived from highly paraffinic crudes have higher V.I. values than lubricating oils derived from highly naphthenic crudes. This difference was used, in fact, to fix the limits of 0 to 100 on the Dean and Davis scale, these values having been assigned, respectively, to a poor naphthene-base oil and a good paraffin-base oil. The operational advantages offered by a lubricant having a high V.I. include principally less friction due to viscous "drag" at low temperatures as well as reduced lubricant loss and lower wear at high temperatures.

V.I. improvers are chemicals which are added to lubricating oils to make them conform more closely to the ideal lubricant defined above. Although a few non-polymeric substances such as metallic soaps exhibit V.I. improving properties, all commercially important V.I. improvers are oil-soluble organic polymers. Suitable polymers exert a greater thickening effect on oil at high temperatures than they do at lower temperatures.. The end result of such selective thickening is that the oil suffers less viscosity change with changing temperature, i.e., its V.I. is raised. It has been proposed that selective thickening occurs because the polymer molecule assumes a compact, curled form in a poor solvent such as cold oil and an uncurled, high surface area form in a better solvent such as hot oil. In the latter form, it is more highly solvated and exerts its maximum thickening effect on the oil.

Commercial V.I. improvers belong to the following families of polymers:

(I) Polyisobutenes (II) Polymethacrylates, i.e., copolymers of various chain length alkyl methacrylates (III) Vinyl acetate - fumaric acid ester copolymers (IV) Polyacrylates, i.e., copolymers of various chain length alkyl acrylates A preferred V.I. improver is an acrylate polymer of the formula

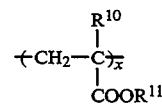

wherein $R^{10}$ is hydrogen or a lower alkyl group containing from 1 to about 4 carbon atoms, $R^{11}$ is a mixture of alkyl, cycloalkyl or aromatic groups containing from about 4 to about 24 carbon atoms, and x is an integer providing a weight average molecular weight (Mw) to the acrylate polymer of about 5000 to about 1,000,000.

Preferably $R^{10}$ is a methyl or ethyl group and more preferably, a methyl group. $R^{11}$ is primarily a mixture of alkyl groups containing from 4 to about 18 carbon atoms. In one embodiment, the weight average molecular weight of the acrylate polymer is from about 100,000 to about 1,000,000 and in other embodiments, the molecular weight of the polymer may be from 100,000 to about 700,000 and 300,000 to about 700,000.

Specific examples of the alkyl groups $R^{10}$ which may be included in the polymers of the present invention include, for example, n-butyl, octyl, decyl, dodecyl, tridecyl, octadecyl, hexadecyl, octadecyl. The mixture of alkyl groups can be varied so long as the resulting polymer is hydrocarbon-soluble.

The following examples are illustrative of the preparations of the acrylate polymers. All parts and percentages are by weight unless indicated to the contrary.

Example (B)(7)-1

Added to a 2 liter 4 neck flask is 50.8 parts (0.20 moles) lauryl methacrylate, 44.4 parts (0.20) isobornyl methacrylate, 38.4 parts (0.20 moles) 2-phenoxy ethyl acrylate, 37.6 parts (0.20 moles) 2-ethylhexyl acrylate, 45.2 parts (0.20 moles) isodecyl methacrylate and 500 parts toluene. At 100° C. 1 parts Vazo ®67 (2,2′ azo-bis(2-methylbutyronitrile)) in 20 parts toluene is added over 7 hours. The reaction is held at 100° C. for 16 hours after which the temperature is increased to 120° C. to remove toluene and added is 216 parts of Sunyl ®80. Volatiles are removed by vacuum distillation at 20 millimeters mercury at 140° C. The contents are filtered to give the desired product.

Example (B)(7)-2

Added to a 2 liter 4 neck flask is 38.1 parts (0.15 moles) lauryl methacrylate, 48.6 parts (0.15 moles) stearyl acrylate, 28.2 parts (0.15 moles) 2-ethylhexyl methacrylate, 25.5 parts (0.15 moles) tetrahydrofurfuryl methacrylate, 33.9 parts (0.15 moles) isodecyl methacrylate and 500 parts toluene. At 100° C. 1 part Vazo ®67 in 20 parts toluene is added dropwise in 6 hours. After the addition is complete, the reaction mixture is held at 100° C. for 15.5 hours, toluene is distilled out and 174 parts Sunyl ®80 is added. The contents are vacuum stripped at 140° C. at 20 millimeters of mercury and filtered to give the desired product.

An example of a commercially available methacrylate ester polymer which has been found to be useful in the present invention is sold under the tradename of "Acryloid 702" by Rohm and Haas, wherein $R^{10}$ is predominantly a mixture of n-butyl, tridecyl, and octadecyl groups. The weight average molecular weight (Mw) of the polymer is about 404,000 and the number average molecular weight (Mn) is about 118,000. Another commercially available methacrylate polymer useful in the present invention is available under the tradename of "Acryloid 954" by Rohm and Haas, wherein $R^{10}$ is predominantly a mixture of n-butyl, decyl, tridecyl, octadecyl, and tetradecyl groups. The weight average molecular weight of Acryloid 954 is found to be about 440,000 and the number average molecular weight is about 111,000. Each of these commercially available methacrylate polymers is sold in the form of a concentrate of about 40% by weight of the polymer in a light-colored mineral lubricating oil base. When the polymer is identified by the tradename, the amount of material added is intended to represent an amount of the commercially available Acryloid material including the oil.

Other commercially available polymethacrylates are available from Rohm and Haas Company as Acryloid 1253, Acryloid 1265, Acryloid 1263, Acryloid 1267, from Rohm GmbH as Viscoplex 0-410, Viscoplex 10-930, Viscoplex 5029, from Societe Francaise D'Organo-Synthese as Garbacryl T-84, Garbacryl T-78S, from Texaco as TLA 233, TLA 5010 and TC 10124.

Some of these polymethacrylates may be PMA/OCP (olefin copolymer) type polymers.

(B)(8) The Aromatic Amine

Component (B)(8) is at least one aromatic amine of the formula

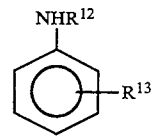

wherein $R^{12}$ is

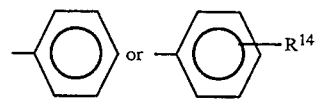

and $R^{13}$ and $R^{14}$ are independently a hydrogen or an alkyl group containing from 1 up to 24 carbon atoms. Preferably $R^{12}$ is

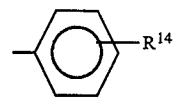

and $R^{13}$ and $R^{14}$ are alkyl groups containing from 4 up to about 20 carbon atoms. In a particularly advantageous embodiment, component (B)(8) comprises an alkylated diphenylamine such as nonylateddiphenylamine of the formula

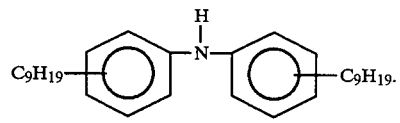

In forming the composition of this invention, components (A) and (B) are mixed together at an (A):(B) weight ratio of from (1–99):(99–1), preferably from (10–90)(90-10) and most preferably from (40–60):(60-40). This mixing can occur at a temperature of from ambient up to the decomposition temperature of any component.

The components of this invention are blended together according to the above ranges to effect solution. The following Tables I and II outline examples so as to provide those of ordinary skill in the art with a complete disclosure and description on how to make the composition of this invention and is not intended to limit the scope of what the inventor regards as the invention. All parts are by weight.

Table I shows the poor oxidation properties of estolides and the improved oxidation properties by including component (B)(1) or components (B)(1) and (B)(2) with component (A). Table II shows the improvement in viscosity at 40° C. and 100 ° C. by the incorporation of component (B)(7) into the estolide component (A).

TABLE I

EFFECTS OF ANTIOXIDANTS ON ESTOLIDES ROTARY BOMB OXIDATION TEST (RBOT)

| EXAMPLE NUMBER | COMPONENT (A) | COMPONENT (B) | RBOT (MINUTES) |
| --- | --- | --- | --- |
| 1 | 100 parts product of example A-4 | None | 16 |
| 2 | 98 parts product of Example A-4 | 2 parts di-t-butylphenol (B)(1) | 76 |
| 3 | 97.95 parts product of Example A-4 | 2 parts di-t-butylphenol (B)(1), 0.05 parts tolyltriazole (B)(2) | 94 |
| 4 | 100 parts product of Example A-3 | None | 16 |
| 5 | 98 parts product of Example A-3 | 2 parts di-t-butylphenol (B)(1) | 79 |
| 6 | 97.95 parts product of Example A-3 | 2 parts di-t-butylphenol (B)(1), 0.05 parts tolyltriazole (B)(2) | 89 |

TABLE II

VISCOMETRICS OF ESTOLIDES WITH AND WITHOUT VISCOSITY INDEX IMPROVERS

| EXAMPLE NUMBER | COMPONENT (A) | COMPONENT (B) | POUR POINT | VISCOSITY 40° C. | VISCOSITY 100° C. | VI |
| --- | --- | --- | --- | --- | --- | --- |
| 1 | 100 parts Product of Example A-4 | None | −42 | 109.72 | 18.93 | 194 |
| 2 | 98 parts Product of Example A-4 | 2 parts Acryloid 1267-3 (B)(7) | −48 | 114.8 | 19.89 | 197 |
| 3 | 98 parts Product of Example A-4 | 2 parts Garbacryl T-84 (B)(7) | −42 | 122.7 | 20.94 | 197 |
| 4 | 98 parts Product of Example A-4 | 2 parts TLA 453 (B)(7) | −48 | 122.1 | 21.15 | 200 |
| 5 | 98 parts Product of Example A-4 | 2 parts Viscoplex 0-410 (B)(7) | −42 | 119.2 | 20.64 | 199 |

The compositions of this invention may contain other additives. The use of such additives is optional, and the presence thereof in the compositions of this invention will depend on the particular use and level of performance required. One optional additive is a zinc salt of a dithiophosphoric acid. Zinc salts of dithiophosphoric acids are often referred to as zinc dithiophosphates, zinc 0,0-dihydrocarbyl dithiophosphates, and by other commonly used names. They are sometimes referred to by the abbreviation ZDP. One or more zinc salts of dithiophosphoric acids may be present in a minor amount to provide additional extreme pressure, anti-wear and anti-oxidancy properties.

In addition to zinc salts of dithiophosphoric acids discussed hereinabove, other additives that may optionally be used in the compositions, additive concentrates and lubricating compositions of this invention include, for example, detergents, dispersants, pour point depressing agents, extreme pressure agents, anti-wear agents, color stabilizers and anti-foam agents.

Pour point depressants are a particularly useful type of additive. See for example, page 8 of "Lubricant Additives" by C. V. Smalheer and R. Kennedy Smith (Lezius-Hiles Company Publishers, Cleveland, Ohio, 1967). Pour point depressants useful for the purpose of this invention, techniques for their preparation and their use are described in U.S. Pat. Nos. 2,387,501; 2,015,748; 2,655,479; 1,815,022; 2,191,498; 2,666,748; 2,721,877; 2,721,878; and 3,250,715 which are expressly incorporated by reference for their relevant disclosures.

Anti-foam agents used to reduce or prevent the formation of stable foam include silicones or organic polymers. Examples of these and additional anti-foam compositions are described in "Foam Control Agents", by Henry T. Kerner (Noyes Data Corporation, 1976), pages 125–162.

Detergents and dispersants may be of the ash-producing or ashless type. The ash-producing detergents are exemplified by oil soluble neutral and basic salts of alkali or alkaline earth metals with sulfonic acids, carboxylic acids, phenols or organic phosphorus acids characterized by at least one direct carbon-to-phosphorus linkage.

The term "basic salt" is used to designate metal salts wherein the metal is present in stoichiometrically larger amounts than the organic acid radical. Basic salts and techniques for preparing and using them are well known to those skilled in the art and need not be discussed in detail here.

Ashless detergents and dispersants are so-called despite the fact that, depending on its constitution, the detergent or dispersant may upon combustion yield at non-volatile residue such as boric oxide or phosphorus pentoxide; however, it does not ordinarily contain metal and therefore does not yield a metal-containing ash on combustion. Many types of known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent No. 1,306,529 and in many U.S. Patents including the following:

| | | |
| --- | --- | --- |
| 3,163,603 | 3,381,022 | 3,542,680 |
| 3,184,474 | 3,399,141 | 3,567,637 |
| 3,215,707 | 3,415,750 | 3,574,101 |
| 3,219,666 | 3,433,744 | 3,576,743 |
| 3,271,310 | 3,444,170 | 3,630,904 |
| 3,272,746 | 3,448,048 | 3,632,510 |
| 3,281,357 | 3,448,049 | 3,632,511 |
| 3,306,908 | 3,451,933 | 3,697,428 |
| 3,311,558 | 3,454,607 | 3,725,441 |
| 3,316,177 | 3,467,668 | 4,194,886 |
| 3,340,281 | 3,501,405 | 4,234,435 |
| 3,341,542 | 3,522,179 | 4,491,527 |
| 3,346,493 | 3,541,012 | RE 26,433 |
| 3,351,552 | 3,541,678 | |

(2) Reaction products of relatively high molecular weight aliphatic or alicyclic halides with amines, preferably polyalkylene polyamines. These may be characterized as "amine dispersants" and examples thereof are described for example, in the following U.S. Patents:

| 3,275,554 | 3,454,555 |
|---|---|
| 3,438,757 | 3,565,804 |

(3) Reaction products of alkyl phenols in which the alkyl groups contain at least about 30 carbon atoms with aldehydes (especially formaldehyde) and amines (especially polyalkylene polyamines), which may be characterized as "Mannich dispersants". The materials described in the following U.S. Patents are illustrative:

| 3,413,347 | 3,725,480 |
|---|---|
| 3,697,574 | 3,726,882 |
| 3,725,277 | |

(4) Products obtained by post-treating the carboxylic amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Patents:

| 3,036,003 | 3,282,955 | 3,493,520 | 3,639,242 |
|---|---|---|---|
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |
| | | | 4,234,435 |

(5) Interpolymers of oil-solubilizing monomers such as decyl methacrylate, vinyl decyl ether and high molecular weight olefins with monomers containing polar substituents, e.g., aminoalkyl acrylates or methacrylates, acrylamides and poly-(oxyethylene)-substituted acrylates. These may be characterized as "polymeric dispersants" and examples thereof are disclosed in the following U.S. Patents:

| 3,329,658 | 3,666,730 |
|---|---|
| 3,449,250 | 3,687,849 |
| 3,519,565 | 3,702,300 |

The above-noted patents are incorporated by reference herein for their disclosures of ashless dispersants.

The above-illustrated additives may each be present in lubricating compositions at a concentration of as little as 0.001% by weight usually ranging from about 0.01% to about 20% by weight. In most instances, they each present at from about 0.1% to about 10% by weight.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:
1. A composition, comprising;
(A) at least one triglyceride estolide of the formula

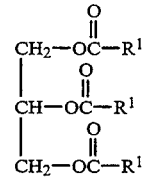

wherein one of the $R^1$ groups is an aliphatic group containing from 9 to 19 carbon atoms and the remaining $R^1$ groups are

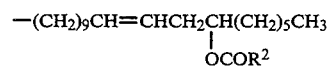

and $R^2$ is a aliphatic group containing from 2 to 24 carbon atoms and
(B) at least one performance additive selected from the group consisting of
(1) at least one alkyl phenol of the formula

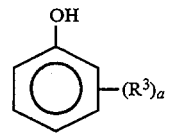

wherein $R^3$ is an alkyl group containing from 1 up to about 24 carbon atoms and a is an integer of from 1 up to 5;
(2) a benzotriazole of the formula

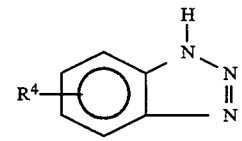

wherein $R^4$ is hydrogen or an alkyl group of 1 up to about 24 carbon atoms;
(3) a phosphatide of the formula

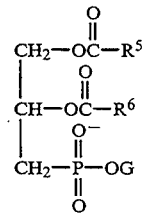

wherein $R^5$ and $R^6$ are aliphatic hydrocarbyl groups containing from 8 to about 24 carbon atoms, and G is selected from the group consisting of hydrogen;

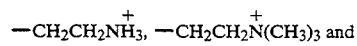

-continued
—CH$_2$CHCOOH
      |
      $^+$NH$_3$ (4) an amine phosphate
(5) citric acid and derivatives of citric acid of the formula

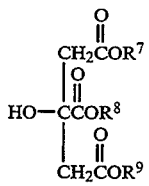

wherein R$^7$, R$^8$ and R$^9$ are independently hydrogen or aliphatic hydrocarbyl groups containing from 1 to about 12 carbon atoms, or an aromatic or substituted aromatic groups containing from 6 to about 50 carbon atoms with the proviso that at least one of R$^7$, R$^8$ and R$^9$ is an aliphatic hydrocarbyl group;
(6) a triphenyl phosphorothionate
(7) at least one viscosity index improver; and
(8) at least one aromatic amine of the formula

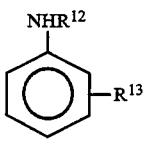

wherein R$^{12}$ is

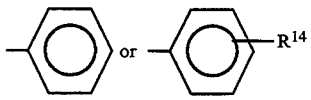

and R$^{13}$ and R$^{14}$ are independently a hydrogen or an alkyl group containing from 1 up to about 24 carbon atoms.

2. The composition of claim 1 wherein R$^2$ is a heptadecenyl group.

3. The composition of claim 2 wherein R$^2$ is an isostearyl group.

4. The composition of claim 1 wherein within (B)(1) a is 2 and R$^3$ contains from 1 up to about 8 carbon atoms.

5. The composition of claim 4 wherein the alkyl phenol is of the formula

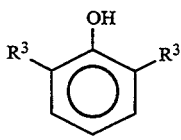

wherein R$^3$ is t-butyl.

6. The composition of claim 1 wherein within (B)(2) R$^4$ is hydrogen or an alkyl group containing from 1 up to about 8 carbon atoms.

7. The composition of claim 1 wherein within (B)(2) R$^4$ is a methyl group.

8. The composition of claim 1 wherein the viscosity index improver (B)(7) is an acrylate polymer of the formula

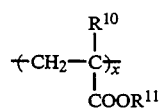

wherein R$^{10}$ is hydrogen or a lower alkyl group containing from 1 to about 4 carbon atoms, R$^{11}$ is a mixture of alkyl, cycloalkyl or aromatic groups containing from about 4 to about 24 carbon atoms, and x is an integer providing a weight average molecular weight (Mw) to the acrylate polymer of about 5000 to about 1,000,000.

9. The composition of claim 8 wherein R$^{10}$ is a methyl group.

10. The composition of claim 8 wherein the molecular weight of the polymer is from about 50,000 to about 500,000.

11. The composition of claim 1 wherein within (B)(8) R$^{12}$ is

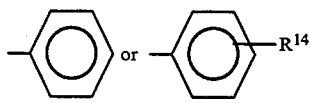

and R$^{13}$ and R$^{14}$ are alkyl groups containing from 4 to 18 carbon atoms.

12. The composition of claim 11 wherein within (B)(8) R$^{13}$ and R$^{14}$ are nonyl groups.

13. A composition, comprising;
(A) at least one triglyceride estolide prepared by reacting a triglyceride containing —OH functionality with a carboxylic acid of the formula R$^2$COOH, HOOCCH=CHCOOH, HOOC(CH$_2$)$_t$-COOH, or Ar(COOH)$_x$ or esters thereof wherein R$^2$ is a aliphatic group containing from 2 to 24 carbon atoms, t is from zero up to 8, Ar is a benzene or naphthalene nucleus and x is 1, and
(B) at least one performance additive selected from the group consisting of
(1) at least one alkyl phenol of the formula

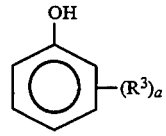

wherein R$^3$ is an alkyl group containing from 1 up to about 24 carbon atoms and a is an integer of from 1 up to 5;
(2) a benzotriazole of the formula

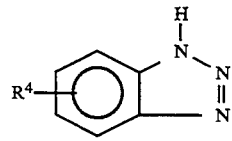

wherein R$^4$ is hydrogen or an alkyl group of 1 up to about 24 carbon atoms;
(3) a phosphatide of the formula

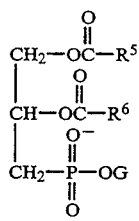

wherein $R^5$ and $R^6$ are aliphatic hydrocarbyl groups containing from 8 to about 24 carbon atoms, and G is selected from the group consisting of hydrogen;

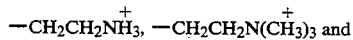

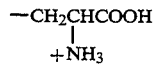

(4) an amine phosphate, (5) citric acid and derivatives of citric acid of the formula

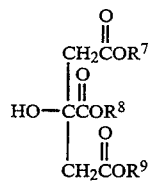

wherein $R^7$, $R^8$ and $R^9$ are independently hydrogen or aliphatic hydrocarbyl groups containing from 1 to about 12 carbon atoms, or an aromatic or substituted aromatic groups containing from 6 to about 50 carbon atoms with the proviso that at least one of $R^7$, $R^8$ and $R^9$ is an aliphatic hydrocarbyl group;

(6) a triphenyl phosphorothionate;
(7) at least one viscosity index improver; and
(8) at least one aromatic amine of the formula

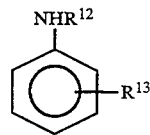

wherein $R^{12}$ is

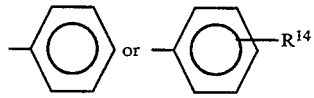

and $R^{13}$ and $R^{14}$ are independently a hydrogen or an alkyl group containing from 1 up to about 24 carbon atoms.

* * * * *